United States Patent

Nguyen et al.

[11] Patent Number: 6,152,939
[45] Date of Patent: Nov. 28, 2000

[54] TONGUE SCRAPER

[76] Inventors: Thuy B. Nguyen; Van Nguyen, both of P.O. Box 70042, Stockton, Calif. 95267

[21] Appl. No.: 09/220,925

[22] Filed: Dec. 24, 1998

[51] Int. Cl.⁷ .................................................. A61B 17/24
[52] U.S. Cl. ............................................................ 606/161
[58] Field of Search .................................... 606/161, 131; 15/111, 100, 143.1; D24/146, 147–150, 176

[56] References Cited

U.S. PATENT DOCUMENTS

| | | | |
|---|---|---|---|
| 194,364 | 8/1877 | Morgenthau | 606/161 |
| 1,893,524 | 1/1933 | Shanley | 606/161 |
| 4,582,059 | 4/1986 | Tiwari | 606/161 |
| 5,569,278 | 10/1996 | Persad | 606/161 |
| 5,868,769 | 2/1999 | Rosenblood et al. | 606/161 |

*Primary Examiner*—Michael Buiz
*Assistant Examiner*—Tan-Uyen T. Ho

[57] ABSTRACT

A tongue scraper for cleaning the tongue of a user. The tongue scraper includes a resiliently flexible strip has first and second faces, a pair of opposite ends, a pair of side edges extending between the ends of the flexible strip, and longitudinal axis extending between the ends of the flexible strip. The flexible strip has a spaced apart pleated regions which divide the flexible strip into a pair of handle portions and a scraping portion interposed between the handle portions.

9 Claims, 3 Drawing Sheets

TONGUE SCRAPER

BACKGROUND OF THE INVENTION

1. Field of the Invention

The present invention relates to tongue scrapers and more particularly pertains to a new tongue scraper for cleaning the tongue of a user.

2. Description of the Prior Art

The use of tongue scrapers is known in the prior art. More specifically, tongue scrapers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,569,278; 5,217,475; 3,683,924; U.S. Pat. No. Des. 360,262; U.S. Pat. No. 3,890,964; and U.S. Pat. No. Des. 378,411.

While these devices fulfill their respective, particular objectives and requirements, the aforementioned patents do not disclose a new tongue scraper. The inventive device includes a resiliently flexible strip has first and second faces, a pair of opposite ends, a pair of side edges extending between the ends of the flexible strip, and longitudinal axis extending between the ends of the flexible strip. The flexible strip has a spaced apart pleated regions which divide the flexible strip into a pair of handle portions and a scraping portion interposed between the handle portions.

In these respects, the tongue scraper according to the present invention substantially departs from the conventional concepts and designs of the prior art, and in so doing provides an apparatus primarily developed for the purpose of cleaning the tongue of a user.

SUMMARY OF THE INVENTION

In view of the foregoing disadvantages inherent in the known types of tongue scrapers now present in the prior art, the present invention provides a new tongue scraper construction wherein the same can be utilized for cleaning the tongue of a user.

The general purpose of the present invention, which will be described subsequently in greater detail, is to provide a new tongue scraper apparatus and method which has many of the advantages of the tongue scrapers mentioned heretofore and many novel features that result in a new tongue scraper which is not anticipated, rendered obvious, suggested, or even implied by any of the prior art tongue scrapers, either alone or in any combination thereof.

To attain this, the present invention generally comprises a resiliently flexible strip has first and second faces, a pair of opposite ends, a pair of side edges extending between the ends of the flexible strip, and longitudinal axis extending between the ends of the flexible strip. The flexible strip has a spaced apart pleated regions which divide the flexible strip into a pair of handle portions and a scraping portion interposed between the handle portions.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tongue scraper apparatus and method which has many of the advantages of the tongue scrapers mentioned heretofore and many novel features that result in a new tongue scraper which is not anticipated, rendered obvious, suggested, or even implied by any of the prior art tongue scrapers, either alone or in any combination thereof.

It is another object of the present invention to provide a new tongue scraper which may be easily and efficiently manufactured and marketed.

It is a further object of the present invention to provide a new tongue scraper which is of a durable and reliable construction.

An even further object of the present invention is to provide a new tongue scraper which is susceptible of a low cost of manufacture with regard to both materials and labor, and which accordingly is then susceptible of low prices of sale to the consuming public, thereby making such tongue scraper economically available to the buying public.

Still yet another object of the present invention is to provide a new tongue scraper which provides in the apparatuses and methods of the prior art some of the advantages thereof, while simultaneously overcoming some of the disadvantages normally associated therewith.

Still another object of the present invention is to provide a new tongue scraper for cleaning the tongue of a user.

Yet another object of the present invention is to provide a new tongue scraper which includes a resiliently flexible strip has first and second faces, a pair of opposite ends, a pair of side edges extending between the ends of the flexible strip, and longitudinal axis extending between the ends of the flexible strip. The flexible strip has a spaced apart pleated regions which divide the flexible strip into a pair of handle portions and a scraping portion interposed between the handle portions.

Still yet another object of the present invention is to provide a new tongue scraper that may be used to scrape debris off of the tongue to provide a healthy oral environment and prevent bad breath and tooth decay.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
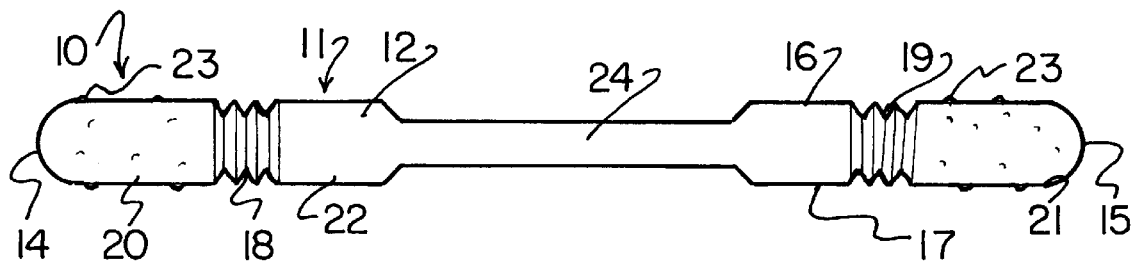
FIG. 1 is a schematic plane view of a preferred embodiment of a new tongue scraper according to the present invention.

With reference now to the drawings, and in particular to FIGS. 1 through 6 thereof, a new tongue scraper embodying the principles and concepts of the present invention and generally designated by the reference numeral 10 will be described.

As best illustrated in FIGS. 1 through 6, the tongue scraper 10 generally comprises a resiliently flexible strip has first and second faces, a pair of opposite ends, a pair of side edges extending between the ends of the flexible strip, and longitudinal axis extending between the ends of the flexible strip. The flexible strip has a spaced apart pleated regions which divide the flexible strip into a pair of handle portions and a scraping portion interposed between the handle portions.

Figure 2:
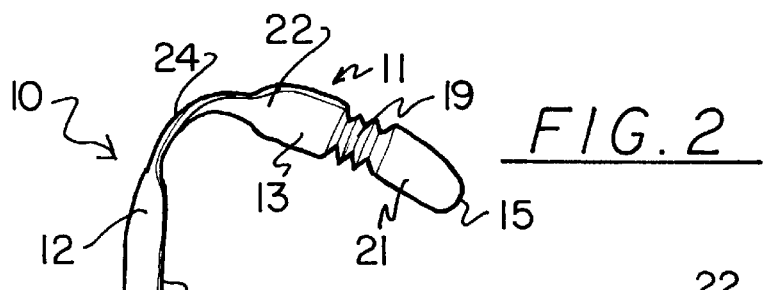
FIG. 2 is a schematic perspective view of the present invention flexed into a curved shape for scraping debris off of the surface of a tongue.

In closer detail, the tongue scraper 10 comprises an elongate resiliently flexible strip 11 having generally flat first and second faces 12,13, a pair of opposite ends 14,15, a pair of side edges 16,17 extending between the ends of the flexible strip, and longitudinal axis extending between the ends of the flexible strip. As illustrated in FIG. 2, the flexible strip is bendable transversely to the longitudinal axis of the flexible strip. Ideally, the flexible strip comprises a resiliently flexible plastic material for preventing fluid from soaking into the flexible strip and weakening the flexible strip. The flexible strip has a length defined between the ends of the flexible strip and a width defined between the side edges of the flexible strip.

The flexible strip has a spaced apart pleated regions 18,19 with each of sad pleated regions having a plurality of accordion folds. The pleated regions are spaced apart from the ends of the flexible strip with a first of the pleated regions positioned towards a first of the ends of the flexible strip and a second of the pleated regions positioned towards a second of the ends of the flexible strip. The pleated regions are preferably about equally spaced apart from the associated adjacent end of the flexible strip.

The pleated regions of the flexible strip divide the flexible strip into a pair of handle portions 20,21 and a scraping portion 22 interposed between the handle portions. The scraping portion is defined between the pleated regions. A first of the handle portions is defined between the first pleated region and the first end of the flexible strip. A second of the handle portions is defined between the second pleated region and the second end of the flexible strip.

The scraping portion and the handle portions each have a length defined along the longitudinal axis of the flexible strip. The length of the scraping portion is defined between the pleated portions. The length of the first handle portion is defined between the first pleated region and the first end of the flexible strip. The length of the second handle portion is defined between the second pleated region and the second end of the flexible strip. The lengths of the handle portions are preferably about equal to one another with the length of the scraping portion being greater than the length of either of the handle portions. In an ideal illustrative embodiment, the length of each of the handle portions is about 1 inch, and the length of the scraping portion is between about 4½ inches and about 6 inches.

In a preferred embodiment, illustrated in FIG. 1, the first and second faces of the flexible strip on each of the handle portions is frictionally enhanced with respect to a smooth surface to aid grip of the fingers of user gripping the handle portions. Preferably, the handle portions in this preferred embodiment each have plurality of resiliently compressible nubs 23 thereon forming the frictionally enhanced faces of the handle portions. Ideally, the nubs comprise a resiliently compressible rubber coating on the handle portions.

In this preferred embodiment, the scraping portion has a narrowed region 24 with the width of the narrowed region being less than the width of the rest of the flexible strip. The first and second faces of the flexible strip taper towards each other at each side edge in the narrowed region such that the side edges of the flexible strip each have a sharpened edge along the associated narrowed region for aiding the scrapping off of debris from the tongue of the user as the side edges in the narrowed regions are scraped across the surface of the tongue of the user.

Figure 3:
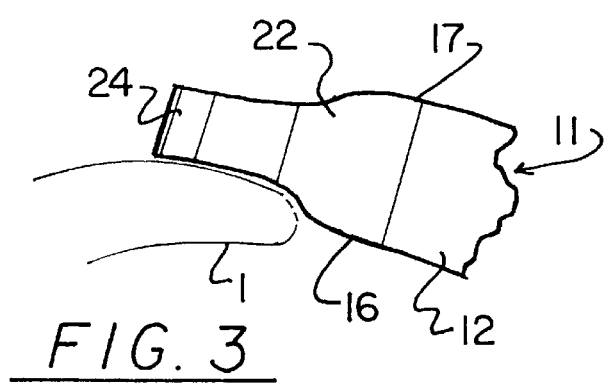
FIG. 3 is a schematic side view of the present invention in use scraping debris off of a tongue.
Figure 5:
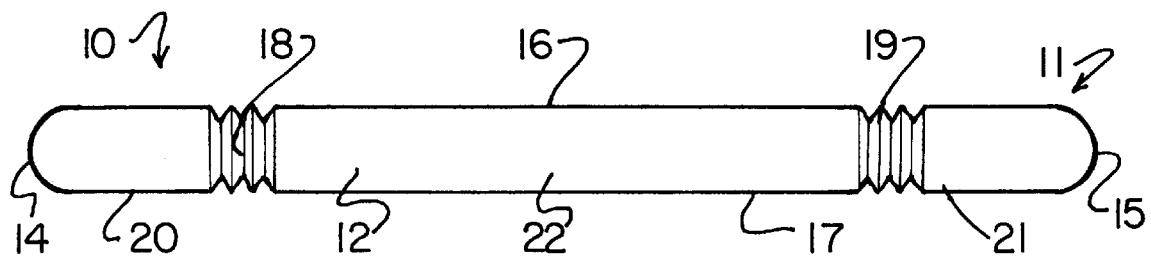
FIG. 5 is a schematic plan view of the present invention.

In use, a user grasps each of the handle portions with their hands and bends the flexible strip into an arcuate shape as illustrated in FIG. 2. The sharpened edge of one of the side edges in the narrowed region is then scraped across the surface of the user's tongue 1 to remove debris from the tongue as illustrated in FIG. 3.

Figure 4:
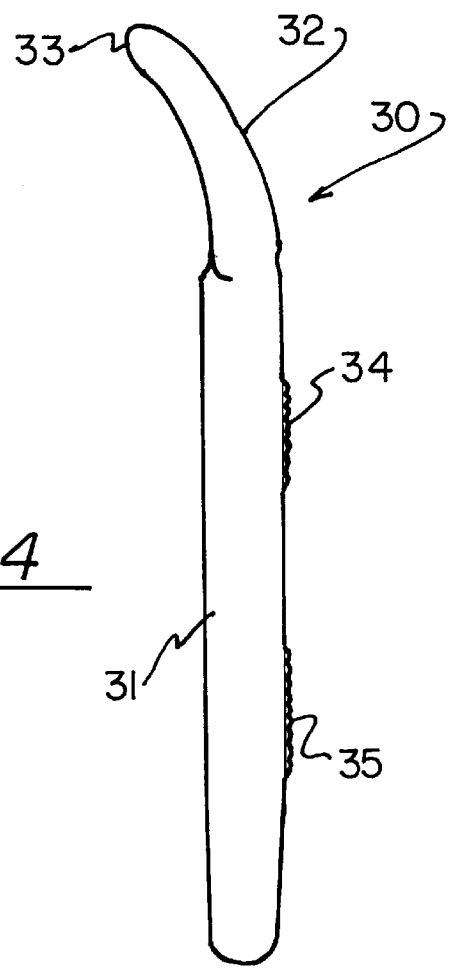
FIG. 4 is a schematic side view of an alternate embodiment of the present invention.
Figure 6:
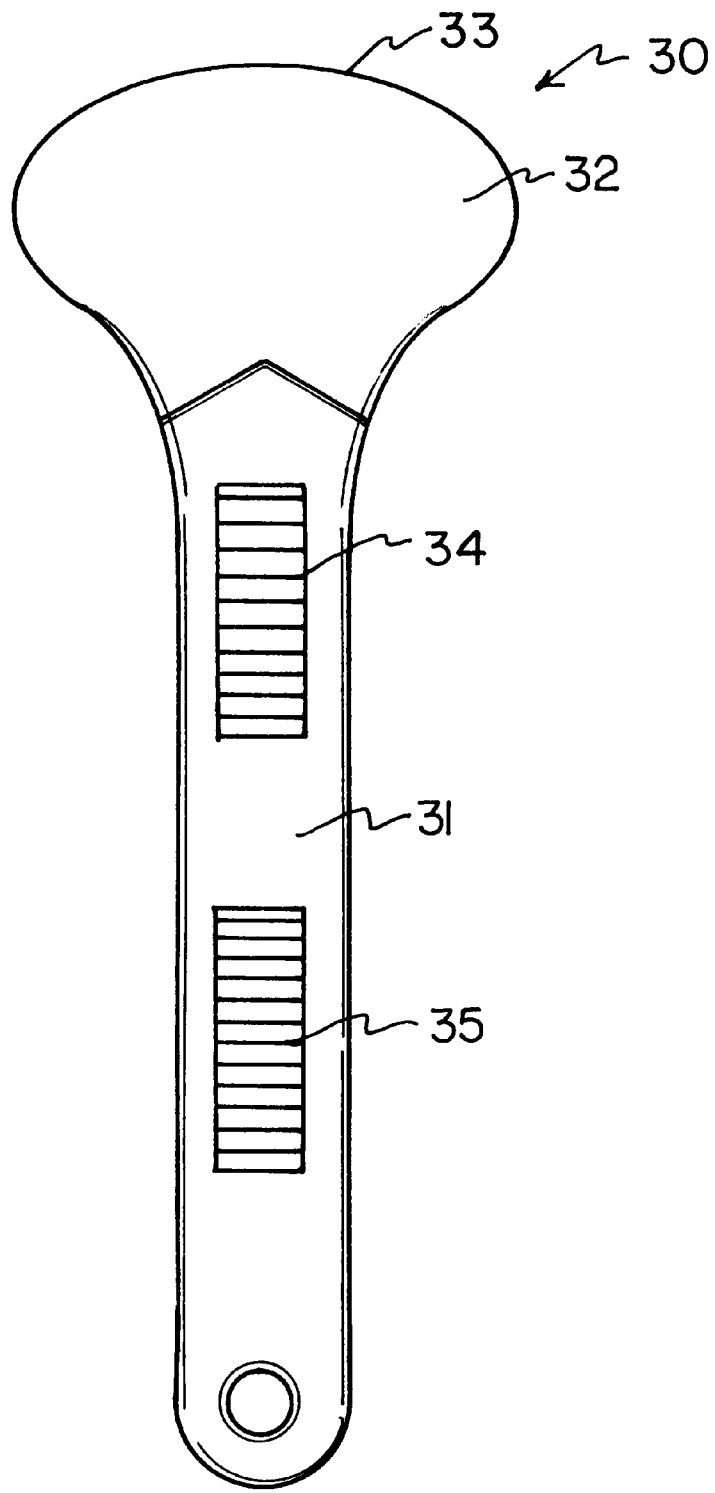
FIG. 6 is a schematic back side view of the alternate embodiment of the present invention.

With reference to FIGS. 4 and 6, another preferred embodiment of the tongue scraper 30 comprises an elongate handle 31 has a pair of opposite ends. A generally oval scraping blade 32 is coupled to one of the ends of the handle. The scrapping blade is curved to resemble the bowl portion of a spoon and has a sharpened scraping edge 33 distal the handle. The handle has a longitudinal axis defined between the ends of the handle. The scraping edge is extended generally perpendicular to the longitudinal axis of the handle. The scraping blade is extended at an acute angle to the longitudinal axis of the handle in a direction outwards from a front side of the handle. In an ideal illustrative embodiment, the scraping blade has a width defined generally perpendicular to the longitudinal axis of the handle of about 2 inches and a length defined in a plane in which the longitudinal axis of the handle lies of about 1 inch. In this ideal illustrative embodiment, the handle has a length defined between the ends of the handle between about 3½ and about 4 inches. Preferably, the handle has a spaced apart pair of resiliently compressible longitudinal grips 34,35 provided an a back side of the handle, the longitudinal grips is designed for aiding the grip of a user grasping the handle. In use, a user grasps the handle and runs the sharpened scraping edge of the scraping blade against the surface of the user's tongue to remove debris from the tongue.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A tongue scraper, comprising:
    a resiliently flexible strip having first and second faces, a pair of opposite ends, a pair of side edges extending between said ends of said flexible strip, and longitudinal axis extending between said ends of said flexible strip;
    said flexible strip having a spaced apart pleated regions; and
    said pleated regions of said flexible strip dividing said flexible strip into a pair of handle portions and a scraping portion interposed between said handle portions.

2. The tongue scraper of claim 1, wherein said flexible strip is bendable transversely to said longitudinal axis of said flexible strip.

3. The tongue scraper of claim 1, wherein said pleated regions are spaced apart from said ends of said flexible strip, a first of said pleated regions being positioned towards a first of said ends of said flexible strip, a second of said pleated regions being positioned towards a second of said ends of said flexible strip, wherein said pleated regions are about equally spaced apart from the associated adjacent end of said flexible strip.

4. The tongue scraper of claim 1, wherein said scraping portion and said handle portions each having a length defined along said longitudinal axis of said flexible strip, said length of said scraping portion being defined between said pleated portions, said length of said first handle portion being defined between said first pleated region and said first end of said flexible strip, said length of said second handle portion being defined between said second pleated region and said second end of said flexible strip, wherein said lengths of said handle portions are about equal to one another, and wherein said length of said scraping portion is greater than the length of each of said handle portions.

5. The tongue scraper of claim 4, wherein said length of each of said handle portions is about 1 inch, wherein said length of said scraping portion is between about 4½ inches and about 6 inches.

6. The tongue scraper of claim 1, wherein said first and second faces of said flexible strip on each of said handle portions are frictionally enhanced with respect to a smooth surface.

7. The tongue scraper of claim 6, wherein said handle portions each have plurality of resiliently compressible nubs thereon forming said frictionally enhanced faces of said handle portions.

8. The tongue scraper of claim 1, wherein said scraping portion has a narrowed region, said first and second faces of said flexible strip tapering towards each other at each of said side edges in said narrowed region such that said side edges of said flexible strip each have a sharpened edge along the associated narrowed region.

9. A tongue scraper, comprising:
    an elongate resiliently flexible strip having generally flat first and second faces, a pair of opposite ends, a pair of side edges extending between said ends of said flexible strip, and longitudinal axis extending between said ends of said flexible strip;
    said flexible strip being bendable transversely to said longitudinal axis of said flexible strip;
    said flexible strip having a length defined between said ends of said flexible strip and a width defined between said side edges of said flexible strip;
    said flexible strip having a spaced apart pleated regions, each of sad pleated regions having a plurality of accordion folds;
    said pleated regions being spaced apart from said ends of said flexible strip, a first of said pleated regions being positioned towards a first of said ends of said flexible strip, a second of said pleated regions being positioned towards a second of said ends of said flexible strip;
    said pleated regions being about equally spaced apart from the associated adjacent end of said flexible strip;
    said pleated regions of said flexible strip dividing said flexible strip into a pair of handle portions and a scraping portion interposed between said handle portions;
    said scraping portion being defined between said pleated regions, a first of said handle portions being defined between said first pleated region and said first end of said flexible strip, a second of said handle portions being defined between said second pleated region and said second end of said flexible strip;
    said scraping portion and said handle portions each having a length defined along said longitudinal axis of said flexible strip, said length of said scraping portion being defined between said pleated portions, said length of said first handle portion being defined between said first pleated region and said first end of said flexible strip, said length of said second handle portion being defined between said second pleated region and said second end of said flexible strip;
    said lengths of said handle portions being about equal to one another, said length of said scraping portion being greater than the length of each of said handle portions;
    said first and second faces of said flexible strip on each of said handle portions being frictionally enhanced with respect to a smooth surface;
    wherein said handle portions each have plurality of resiliently compressible nubs thereon forming said frictionally enhanced faces of said handle portions;

said scraping portion having a narrowed region, said width of said narrowed region being less than said width of said flexible strip; and said first and second faces of said flexible strip tapering towards each other at each of said side edges in said narrowed region such that said side edges of said flexible strip each have a sharpened edge along the associated narrowed region.

* * * * *